United States Patent [19]

Hayashi et al.

[11] Patent Number: 5,248,597

[45] Date of Patent: Sep. 28, 1993

[54] METHOD AND APPARATUS FOR ANALYZING STARCH AND RELATED CARBOHYDRATES

[75] Inventors: Ryuzo Hayashi, Higashiosaka; Yoshio Hasizume, Akashi; Akio Kariyone, Kyoto, all of Japan

[73] Assignee: Kanzaki Paper Mfg. Co., Ltd., Tokyo, Japan

[21] Appl. No.: 682,953

[22] Filed: Apr. 10, 1991

[30] Foreign Application Priority Data

Apr. 10, 1990 [JP] Japan .................... 2-95953

[51] Int. Cl.⁵ .................... C12Q 1/54; C12Q 1/40; C12M 1/40
[52] U.S. Cl. .................... 435/14; 435/22; 435/288; 210/632
[58] Field of Search .................... 435/14, 22, 288; 210/632

[56] References Cited

U.S. PATENT DOCUMENTS

4,102,745  7/1978  Thompson .................... 195/31 R

FOREIGN PATENT DOCUMENTS

0335167  10/1989  European Pat. Off. .

OTHER PUBLICATIONS

Marro-Vega, G.A., Determination of Mono and Oligosacchar . . . Anal Chem 1989 61 831-838.
Marro-Vega G.A., Post-Column Derivaziation . . . Anal Chem Acta 234 (1990) 13-29.
Emneus J., Flow System for Starch Determination . . . Anal Chem 1990 62, 263-268.
Analytica Chimica Acta vol. 230, No. 1, Mar. 1, 1990, Amsterdam NL, pp. 75-82, T. Ideda et al., "Amperometric response to reducing carbohydrates of an enzyme electrode based on oligosaccharide dehydrogenase, Detection of lactose and alpha-amylase".

Primary Examiner—Michael G. Wityshyn
Assistant Examiner—Ralph Gitomer
Attorney, Agent, or Firm—Wenderoth, Lind & Ponack

[57] ABSTRACT

A method and apparatus for the determination of the average molecular weight, average chain length or dextrose equivalent of starch and related carbohydrates containing glucose units. The starch is analyzed by determining the free glucose amount (Gf) contained in starch or related carbohydrate sample, determining a gross glucose amount (Gt) rendered by hydrolysis of starch or related carbohydrates, and further determining a glucose amount (Gr) rendered by hydrolysis of a reduced product which is obtained by reduction of reducing terminals contained in starch or related carbohydrate.

The average molecular weight, average chain length or dextrose equivalent of the starch is determined using the formulas stated below from the measured amounts of the free glucose amount (Gf), and the glucose amount (Gr). The apparatus preferably utilized immobilized enzymes to conduct the hydrolysis of the starch sample, contains a device for recognizing and storing the measured values and computed data, and contains further a device for computing average molecular weight (Ma), average chain length (Dp) or dextrose equivalent value (DE) according to the following expressions:

$Dp = 2 \cdot Gt/(Gt - Gr + Gf)$,
$Ma = 18(19 \cdot Gt + Gf - Gr)/(Gt - Gr + Gf)$,
$DE = 1000(Gt - Gr + Gf)/(19 \cdot Gt - Gr + Gf)$, or
$DE = 1000/(9 \cdot Dp + 1)$.

24 Claims, 3 Drawing Sheets

METHOD AND APPARATUS FOR ANALYZING STARCH AND RELATED CARBOHYDRATES

BACKGROUND OF THE INVENTION

1. Field of the Invention

This invention relates to the art for determining the average molecular weight (Ma), average chain length (Dp) or dextrose equivalent (DE) value of starch and/or its related carbohydrates, including a polysaccharide or oligosaccharide containing glucose units, with convenience and high accuracy. The related carbohydrates may be hydrolysates from starch, including linear maltooligosaccharides like maltose, maltotriose, maltotetraose, maltopentaose, maltohexaose, maltoheptaose, or derivatives of starch or their hydrolysates, for example, ether derivatives, cationic derivatives, carboxyl derivatives. The invention is especially designed for use in the measurement of for example, sweetening agents corn syrup, food additives, and other industrial materials.

2. Description of Related Art

Starch and its related carbohydrates (hereinafter, the term "starch" will often be used to represent not only starch but also its related carbohydrates have been widely used a material or additive for manufacturing food, paper making, and other various industrial products. In such industrial applications of starch, it is important to the molecular weight (MW) of the starch to have an indication of its properties. For example, the molecular weight (MW) of a starch in a solution affects the viscosity of the starch solution, the hygroscopic property, in its sweetness in the case of corn syrup. Conventional methods for determining the molecular weight (MW) of a starch have been by measurement of intrinsic viscosity, light scattering, osmotic pressure, or speed liquid chromatography of the sample or by quantitative determination of the reducing terminals contained in starch. Of these methods the intrinsic viscosity method and the light scattering method include complicated processes to prepare the sample for measurement and the take a long time to complete a measurement. The osmotic pressure method is likely to be influenced the concentration of salt in the sample, and it is necessary to be careful in preparing the sample for this measurement method. Therefore these methods have been rarely employed except at the basic pre-industrial research stage. The high speed liquid chromatography is method versatile in determining average molecular weight (MW) as well as molecular weight distribution weight (MW) of a starch, but this method requires a standard sample for molecular weight (MW) determination, a complicated process for preparing sample to be measured and a relatively expensive apparatus, not to mention the method is time consuming. Accordingly, this method is also unsuited to industrial application.

Consequently, the most convenient method is the quantitative measurement of reducing terminals which includes a determination of total amounts of the reducing terminals and glucose units contained in a starch sample, and then a ratio of these two measurements if formed to represent the molecular weight (MW) of the starch. In the conventional art of determining the total glucose units, a determination of gross carbohydrate by the phenol and sulfuric acid method has been used, wherein strong acidic and alkaline chemicals are involved and heating is occasionally necessary. These factors pose problems in the disposition of waste chemical liquid and also are hazardous in operation. In view of such situations, for the sake of convenience, in the case where an outstanding starch solution does not contain any chemicals other than carbohydrates, the dried weight thereof was used as a substitute for the gross sugar amount. Thus, the DE value as the index of molecular weight is derived from forming a ratio between the dried weight as noted above and the quantitative amount of reducing terminals. However, actually starch is hygroscopic and this makes it difficult to know the correct dry weight.

Some of the methods for determining the amount of reducing terminals are to use organic agents which react to the reducing terminals and to use oxidation and reduction of ions such as Fe ions and Cu ions. Of these, above all, oxidation and reduction of Cu ion defines the best basis of measurement. That is, when divalent copper ions and a reducing sugar are heated in an alkaline solution, the copper is reduced to the monovalent state which may be quantitatively measured by colorimetry, spectophotemetry, or titration. However, this method has the disadvantage of heating a mass of an alkaline solution, a hazardous operation, and of producing a mass of waste liquid including copper. In addition, while the reducing sugar acts on the Cu ions by reduction, oxygen in the air tends to dissolve into the reacting solution, which causes re-oxidation of monovalent Cu ions. Thus, an error is produced. Requirements for preventing such an error includes a quick operation, sufficient skill, but actually the human error is significant.

Through the description above, it is clear that a means for determining the average molecular weight (MW), average chain length [hereinafter will be often referred to as molecular weight (MW) or equivalent] or DE value of a starch has a large industrial significance and that the need of a method and apparatus for determining this information with convenience and accuracy is presently needed.

SUMMARY OF THE INVENTION

As noted in the beginning of the specification, the term "starch" will often be used to represent not only starch, but also its related carbohydrates including hydrolysates from starch and derivatives, of starch or its hydrolysates, for the sake of simplicity.

An object of the invention is to provide a method and apparatus for determining the molecular weight (MW) or equivalent of starch with convenience and accuracy, wherein the use of metal ions and strong acidic or strong alkaline chemicals are eliminated. Other objects and advantages will be understood from the description hereinbelow.

Particularly, in determining the molecular weight (MW) or equivalent thereof of a starch, this invention employs an enzyme electrode or a combination of an immobilized enzyme column and an electrode which features specificity and high speed, thereby solving the problems of conventional methods in convenience, accuracy and promptness.

More particularly, this invention employs an immobilized enzyme electrode or a combination of an immobilized enzyme column and an electrode to determine a gross glucose amount contained in the hydrolysis from a starch, referred to as step (i), and to determine the glucose amount contained in the hydrolysates from a starch in which the reducing terminals have been beforehand reduced, referred to as step (ii). As step (iii), this invention includes calculation of the average molecular weight Ma, average chain length Dp, or DE value based on the measurements in the steps (i) and (ii).

In the invention, in reducing the reducing terminals of the starch, the use of a compound of borohydride is preferable. In hydrolyzing the starch. Either in step (i) without reduction or in step (ii) subsequent to the reduction, the use of amylase or the joint use of glucosidase and amylase is preferable.

Further, this invention includes the art of employing a device provided with an immobilized enzyme electrode or combination of an immobilized enzyme column and an electrode (a) for achieving measurement of the free glucose amount, and (b) for achieving hydrolysis of a sample starch to determine the gross glucose amount, and (c) for achieving hydrolysis of the sample starch in which the reducing terminals have been beforehand reduced, to determine the gross glucose amount subsequent to the reduction, and (d) calculation of the average molecular weight (MW), average chain length Dp, and DE value based on the measurements of the free glucose amount and glucose amounts with and without reduction.

In the invention the free glucose amount (Gf) of the sample, the gross glucose amount without the reduction (Gt) and the glucose amount subsequent to the reduction (Gr) are determined. The apparatus of this invention includes means for storing these data, from which the average molecular weight Ma, average chain length Dp, and De value are calculated by the formulas indicated below as [7], [6], [9], or [10], respectively:

$$Dp = 2 \cdot Gt/(Gt - Gr + Gf) \quad [6]$$

$$Ma = 18(19 \cdot Gt + Gf - Gr)/(Gt - Gr + Gf) \quad [7]$$

$$DE = 1000(Gt - Gr + Gf)/(19 \cdot Gt - Gr + Gf) \quad [9]$$

$$DE = 1000/(9 \cdot Dp + 1) \quad [10]$$

BRIEF DESCRIPTION OF THE DRAWINGS

Other and further objects, features, and advantages of the invention will be more explicit from the following detailed description taken with reference to the drawings wherein.

DETAILED DESCRIPTION OF THE PREFERRED EMBODIMENTS

Now referring to the drawings, the preferred embodiments of the invention are described below.

A.

First, the process of hydrolyzing starch to determine a gross amount of glucose (Gt) will be described. This invention uses a decide including an enzyme electrode or combination of an immobilized enzyme column and an electrode for measuring glucose.

For hydrolysis, acidic hydrolysis may be applied, but this method requires heating at a high temperature of about 120° C. for several hours, and thus this method is prone to cause decomposition of glucose and thus a good recovery rate is difficult to achiever. Therefore, enzymatic hydrolysis is preferable.

In enzymatic hydrolysis of starch, the use of amylase or joint use of glucosidase and amylase is preferable.

As for the species of amylase, $\alpha$-amylase (EC. 3. 2. 1. 1) of glucoamylase (EC. 3. 2. 1. 3) are preferable. Of these, glucoamylase is especially preferable because it works with a large decomposition rate and the enzyme itself is stable. However, glucoamylase lowers its activity to starch having shorter chain length. For compensation, $\alpha$-glucosidase (EC. 2. 2. 1. 20) having good activity to oligo sugars is preferably added. Also, as for samples which have a high molecular weight and are difficult to dissolve, the use of both $\alpha$- amylase and glucoamylase is preferred because it prevents the retrogradation of starch in hydrolysis.

An enzyme electrode for measuring the gross amount of glucose is not particular or restricted, but it may be constructed by disposing an oxygen electrode or hydrogen peroxide electrode with placement close thereto of glucose oxidase (EC. 1. 1. 3. 4) or pyranose oxidase (EC. 1. 1. 3. 10) in immobilized form. An apparatus incorporating the enzyme electrode may be of the batch type or flow type or other arrangements. Of these, a flow type apparatus incorporating an enzyme electrode capable of detecting hydrogen peroxide is preferable from the standpoint of high speed and accuracy. Also preferable is a flow type measurement apparatus, containing a column type reactor including an immobilized glucose oxidase or pyranose oxidase and having arranged downstream thereof an oxygen electrode or hydrogen peroxide electrode.

A.

Next, the process for determining the amount of glucose (Gr) produced by hydrolysis subsequent to reducing the reducing terminals of starch. In this invention, the measurement of gross glucose is limited to carbohydrates and therefore there is no need to be cautious to the possible impediment of such measurement by oxygen as compared to the case of determining the reduction amount of Cu ions. For the purpose of finding now much the carbohydrate has changed, measurement on a decrease of the carbohydrate is acceptable by oxidizing the reducing terminals, whoever the reduction method is preferable to be free from the problem of a waste liquor containing a compound such as copper. Then, reduction of the reducing terminals of carbohydrates may be carried out by the way of a catalyzer and hydrogen gas or by the way of adding a hydride compound. Of these, the use of a borohydride compound is preferable from the standpoint that a final decomposed product is boric acid and thereby the problem of waste liquor is solved. Wherein it is found that boric acid of practical concentration under which this invention is carried out does not have any unfavorable effect an an enzyme electrode and that the reduction rate is fast to effect prompt processing. In borohydride compounds, water soluble compounds such as sodium borohydride, potassium borohydride may be used.

In carrying out the reduction with the use of these compounds, it is allowable to put a borohydride compound, solid as it is, into a water solution containing a starch sample, or to dissolve the borohydride compound in water or lower alcohol beforehand so that a liquid form of the borohydride compound may be put into the solution containing the starch sample. In the latter case, the decomposition of the borohydride compound takes place gradually with time, which factor accordingly recommends that a compound solution is better to be prepared just before actual use. Decomposition of a borohydride compound is promoted in an acidic condition, which may be cause incompletion of the reduction. Therefore, it is preferable to keep the pH value of the solution of the starch sample in the neutral or alkaline range. As for the amount of the borohydride compound, an amount of the compound to be added should be equal to or more than the molar balance to possible existing amount of reducing sugar. However, should the charged amount be much in excess, the presence of the remaining amount ascribed from the excessive charge of the borohydride compound will possibly impede subsequent analysis, and therefore an excess from 2 to 10 times may be preferable. This reducing reaction proceeds at room temperature, though, heating up to 30° to 100° C. is desirable to promote the reaction. Normally the reaction at about 50° C. takes about 5 min. for completion.

In turn, the reduced product thus obtained in subjected to hydrolysis. At this stage, if an excess of borohydride compound should be present, glucose that is generated would be reduced further, which renders the measurement to be unreasonably lower. In order to avoid this possible trouble, the solution is preferably made acidic beforehand to decompose the existing borohydride compound, for which purpose titration of a dilute hydrochloric acid. 1N HCl solution, for example, is recommended.

In the process of hydrolyzing a reduced starch or related carbohydrates, use of an enzyme-based chemical means is preferable likewise in the step of determining a gross glucose amount. It is to be noted here that at the reduced state, reduced starch or carbohydrates take a malititol structure. It is impossible for both α-amylase and glucoamylase to cut the α-1, 4 linkage resident in malititol molecules. Therefore, measurement of a glucose amount subsequent to hydrolysis by amylase is equivalent to the amount subtracting 2 times of a glucose in reducing terminal from a gross amount of glucose at the state prior to the reduction. It is likened to raise a sensitivity twice in measurement.

In the case where it is necessary to directly find an amount of reducing terminals which is derived by subtraction of a glucose amount generated by hydrolysis subsequent to the reduction, from a gross glucose amount at the state prior to the reduction, joint use of α-glucosidase is recommended. Particularly, α-glucosidase produced by yeast has relatively lower specificity and catalytic activity for hydrolysis of malititol compounds.

C.

Described in the following is the process for calculating average molecular weight (MW), average chain length Dp or DE value based on a gross glucose amount prior to the reduction and a gross glucose amount subsequent to the reduction. These results may be derived from measurements on the steps noted above.

The following example refers to the case where glucoamylase is used for the hydrolysis. It is assumed that Gt indicates the number of moles of a gross glucose prior to the reduction, and that Gr indicates the number of moles of a glucose produced by the hydrolysis subsequent to the reduction. First, the number of moles of reducing terminals R is given, with consideration that malititols are not hydrolyzed through glucoamylase subsequent to the reduction, as follows:

$$R = (Gt - Gr)/2 \qquad [1]$$

The average chain length Dp is determined by division of the gross glucose mole number Gt with R as follows:

$$Dp = 2 \cdot Gt/(Gt - Gr) \qquad [2]$$

Based on the above and on the fact that a glucose unit which has condensed to remove a water molecule has the average molecular weight (MW) 162, average molecular weight Ma of a sample starch or carbohydrate is given as follows:

$$Ma = 162 \cdot Dp \qquad [3]$$

DE value is a value which is derived basically by the multiplication of 100 times the ratio of glucose equivalent amount of a reducing sugar in relation to the total solid amount, which leads to the following expression.

$$DE = 100(Gt - Gr)180/2 \cdot 162 \cdot Gt \qquad [4]$$

These expressions from [1] to [4] are justified if no free glucose is contained.

Accordingly, it is to be noted here that some correction factor should be taken into account if free glucose is contained considerably in a sample, for example, partial hydrolysates of starch.

As for free glucose, a sample starch or carbohydrate is diluted into a solution, which is analyzed with use of an enzymatic electrode for measuring glucose, thereby the amount of free glucose (Gf) is determined. Then, the molar number of reducing terminals is given likewise the expression [1] as below:

$$R = \{(Gt - Gf) - Gr\}/2 + Gf$$

The above leads to:

$$R = (Gt - Gr + Gf)/2 \qquad [5]$$

The average chain length Dp is modified as below:

$$Dp = 2 \cdot Gt/(Gt - Gr + Gf) \qquad [6]$$

The average molecular weight Ma with accuracy is given as below:

$$Ma = (342(R - Gf) + 162 \cdot Gr + 180 \cdot Gf)/R$$

The above leads to:

$$Ma = 18(19 \cdot Gt + Gf - Gr)/(Gt - Gr + Gf) \qquad [7]$$

Likewise, amount of all solid components Ts may be determined.

$$Ts = 180 \cdot Gf + 342(R - Gf) + 162 \cdot Gr$$

The above leads to:

$$Ts = 9(19 \cdot Gt - Gr + Gf) \qquad [8]$$

In turn, De value is modified as below:

$$DE = (180 \cdot R/Ts) \times 100$$

The above leads to:

$$DE = 1000(Gt - Gr + Gf)/(19 \cdot Gt - Gr + Gf) \quad [9]$$

The above is represented as follows:

$$DE = 1000/(9 \cdot Dp + 1) \quad [10]$$

DE value is practically acceptable when characterization or quality control of carbohydrates is intended, but in research purposes, average chain length Dp is often used, wherein Dp multiplied by molecular weight of structural unit or monomer gives an average molecular weight of a polysaccharide. As has been known, many characteristics of high polymers are related to the average molecular weight, and therefore determination of Dp is significant. Formula [10] is significant in interpreting DE in a research sense.

As is understood from the methods and calculations noted above, the art of the present invention does not affect from coexistence of reducing sugar; galactose, fructose, and further is not influenced by coexistence of any salt derived from other than starch or carbohydrates, because the enzyme decomposes only carbohydrates mainly made of glucose. Non affection provides advantage of the present invention. In addition, glucoamylase does not effect to linkages except $\alpha-1,4$ and $\alpha-1,6$-glucoside, and thereby coexistence of sucrose and the like compounds does not impede to the measurements. Needless to mention, in the case that a sample does not include compounds except a starch and the related carbohydrates, it is possible to calculate a ratio of the amount of reducing terminals to the absolutely dried weight.

The art as described herein is utilized to analysis on polymerization degrees of polysaccharides made of glucose; pullulan, dextran, for example, by conversion of enzymatic reactions to be applied to the hydrolysis. In the case of pullulan, pullulanase (EC 3. 2. 1. 41) which will break $\alpha-1,6$ linkage and glucoamylase which will break $\alpha-1,4$ are recommended to be jointly used, thereby degradation down to glucose unit is feasible. Therefore, (i) a sample was subjected to complete degradation to glucose and its glucose concentration is determined, and then (ii) similar operations including the same degradation subsequent to reduction of reducing terminals will bring similar results to those found on starch. Glucoamylase will break $\alpha-1,6$ linkage though, its rate is slow as compared to activity on $\alpha-1,4$ linkage, and therefore the joint use with pullulanase is practical.

In the case of dextran, dextanase (EC 3. 2. 11) will enable degradation down to glucose and therefore similar analysis is feasible. Dextran and pullulan are popular polysaccharides produced by microorganism.

Further, the invention is enabled to carry out analyzing of polysaccharide obtained by reacting other monomers, wherein an enzyme electrode for measuring glucose is altered. It is also possible to measure other polysaccharide by the combination of polysaccharide decomposing enzyme and electrode. Taking galactan contained in plants as an example, amount of DE value equivalent (wherein DE value itself is originally defined in regard to starch and the related carbohydrates) of galactan is enabled to be calculated by combining hydrolase which has an activity to cut galactoside linkage and an immobilized galactose oxidase electrode.

In the same way, analysis of cellooligosaccharide which has mainly $\beta-1,4$ linkage is enabled to be hydrolyzed by employing highly activated species of cellulose which will hydrolyze cellulose into glucose. In this case, the glucose electrode is employed.

D.

Although calculations as noted above are feasible manually, equipment of suitable data store device and computation mechanism with the apparatus for measurements will facilitate convenient, prompt performance of analytical work.

For such purpose, this invention includes the art of employing an apparatus provided with an immobilized enzyme electrode or combination of an immobilized enzyme column and an electrode (1) for achieving measurement of free glucose amount contained in starch, (2) for determination of glucose amount derived from hydrolysis of the starch, and (3) for determination of glucose amount of the starch subsequent to reduction. And apparatus of this invention further has means to calculating molecular weight (MW) or equivalent based on free glucose amount, glucose amounts with and without reduction. Therein the apparatus has means for storing these data, from which average molecular weight Ma, average chain length Dp, and DE value are calculated by equations indicated as [7], [6], [9], and [10] as noted above.

Figure 2:
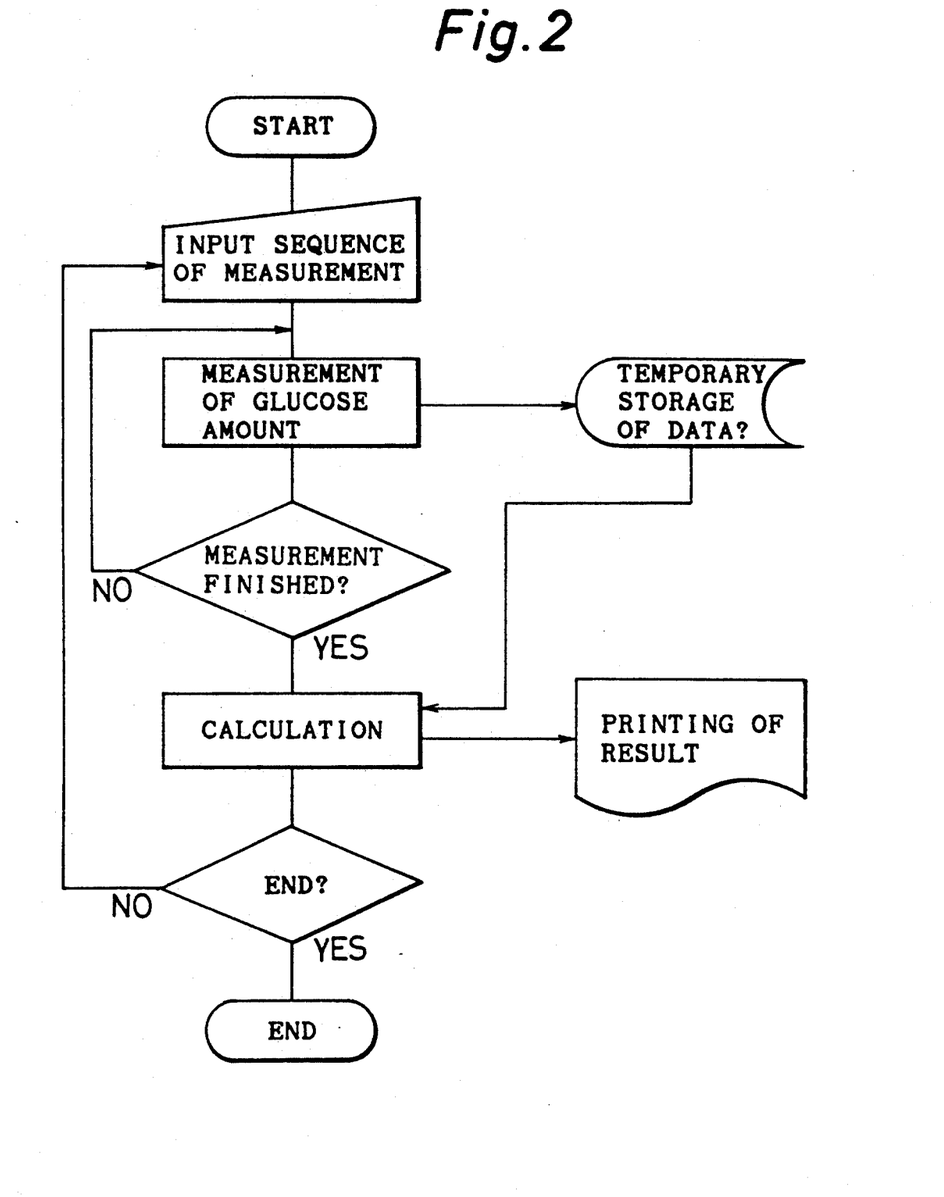
FIG. 2 is a flow map for the sequence of actions in the analysis.

Referring briefly to mechanism for calculations, detected values on current by the electrodes are converted by the potentiostat into voltages, which are stored as data subsequent to A/D conversion, wherein calculations according to the expressions noted above are performed with such a choice as items of measurement may be conformed afterwards or start of calculations is made to coincide with completion of the measurement following previous instruction as to what sequence should be kept. The flow map referring to measurements and calculations is shown in FIG. 2 as will apparent later. Therein, if each measurement item has different dilution factor, mechanism for correction will be added to the calculation mechanism.

These sequential processings may be carried out by a single board computer. Alternative is that data are transferred to a personal computer wherein data are processed by programs, wherein data may be stored in magnetic memory medium.

Description of Preferred Examples

EXAMPLE 1

Apparatus for Measurement

Figure 1:
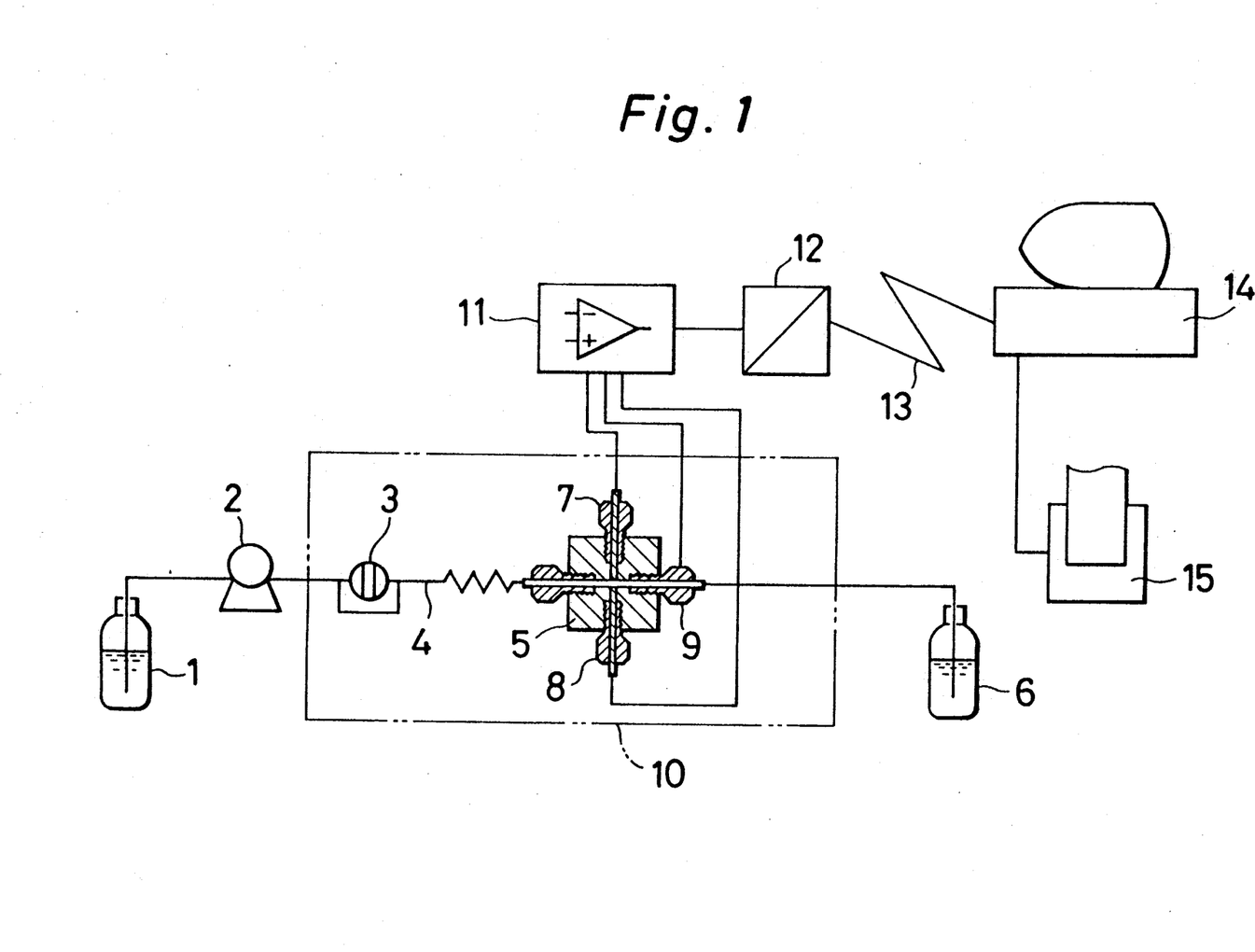
FIG. 1 is a schematic drawing of the flow type measurement apparatus of this invention which is employed in the examples 1 and 2.

Measurements of glucose concentrations were carried out by the flow type apparatus as shown in FIG. 1, wherein a pump (2) for the high speed liquid chromatography was used to feed a 100 mM sodium phosphate buffer solution (1) (pH 6.0) at a rate of 1.0 ml/min. A sample to be analyzed was injected with use of an injector (3). The injected sample was designed to flow, through a pipe (4) made of fluorocarbon resin having an inner diameter=0.5 mm and length=1.0 m, to a measurement cell (5) which was connected to an injector, and thence to a waste bottle (6). The measurement cell was mounted with an enzyme electrode (7) for measurement of glucose on which glucose oxidase was immobilized with bovine serum albumin, an Ag/AgCl reference electrode (8), and a counter electrode (9), and the cell was received in a thermostat (10) to be kept at a temperature range $37°\pm 0.2°$ C.

With use of a potentiostat (11), the enzyme electrode is impressed $\pm 0.6$ V for the reference electrode, and thereby output current values from the enzyme electrode were transferred, after digitizing by an A/D converter (12), to a personal computer (14) through a cable (13). Recording and analysis were carried out in the computer (14) and results were printed out by a printer (15).

Measurement Of Free Glucose

A solution of 1.00 ml was transferred into a test tube from each of the following samples (G1 to G7), into which distilled water of 4.00 ml was added. These diluted samples were fed to the glucose sensor apparatus, and measured glucose concentrations were multiplied 5 times which was assumed as a free glucose amount (Gf) of each of samples (G1 to G7) as below:

| | |
|---|---|
| 50.0 mM glucose | G1 |
| 25.0 mM maltose | G2 |
| 16.7 mM maltotriose | G3 |
| 12.5 mM maltotetraose | G4 |
| 10 mM maltopentaose | G5 |
| 8.33 mM maltohexaose | G6 |
| 7.14 mM maltoheptaose | G7 |

Measurement Of Gross Glucose Amount

Each solution through G1 to G7 of 1.00 ml was transferred into a test tube, into which glucoamylase (derived from *Aspergillus niger*, purchased from SIGMA Co.) of 5 μl, 1000 mM citric acid buffer solution (pH=5.0) of 3995 μl were added and the resultant solution was kept at 37° C. for 1 hour. Glucoamylase will liberate glucose step by step by cutting thereof at non-reducing terminal side of glucose chain. The samples thus prepared was fed into the glucose sensor apparatus and measured glucose concentration was multiplied 5 times, which was assumed to be the gross glucose amount Gt for each of G1 to G7.

Measurement Subsequent to Reduction by Sodium Borohydride

Each solution from G1 to G7 of 1.00 ml was transferred into a test tube, whereinto 0.1 g/ml sodium borohydride solution of 100 μl was added and then kept in 37° C. water bath for 15 min. After completion of the reduction, unreacted sodium borohydride was decomposed by addition of 1N hydrochloric acid 500 μl. Thereinto glucoamylase of 5 μl and 100 mM citric acid buffer solution (pH=5.0) were added to become 5.00 ml solution, with which glucose was obtained through reaction at 37° C. for 30 min. This solution was injected to the glucose sensor apparatus and a resultant glucose concentration was multiplied 5 times, by which it is assumed that glucose amount subsequent to reduction Gr is obtained with G1 to G7 solutions.

Determination Of Average Chain Length And DE Value

Respective data resulted in the analyses were assigned into the equation [6] to calculate the average chain length, and by assignment the data into the equation [9], DE values were calculated, as shown in Table 1.

Theoretical DE values calculated from molecular formulas of G1 to G7 and from experimental values are found to agree each other with a correlation coefficient 0.999 or more. As for the average chain length, experimental results agree to the other with a correlation coefficient 0.999 or more.

TABLE 1

| | Theo. CL | Theo. DE | Exp. aCL | Exp. DE |
|---|---|---|---|---|
| G1 | 1 | 100 | 1.00 | 100 |
| G2 | 2 | 52.6 | 2.00 | 52.6 |
| G3 | 3 | 35.7 | 2.95 | 36.3 |
| G4 | 4 | 27.0 | 3.91 | 27.6 |
| G5 | 5 | 21.7 | 4.88 | 22.3 |
| G6 | 6 | 18.2 | 6.09 | 17.9 |
| G7 | 7 | 15.6 | 6.90 | 15.8 |

Wherein: Theo. indicates theoretical; Exp. experimental; CL chain length; aCL average chain length.

EXAMPLE 2

Five (5) samples were prepared each having a DE value as below, measured by Lane Eynon method which is representative of methods including oxidation and reduction of copper. DE values: 30.0, 32.5, 35.0, 37.5, 40.0. These samples were found by liquid chromatography to contain glucose polymers having various chain lengths. The samples were diluted into water solutions of 1% (wt/vol) and then subjected to experiments and sequential calculations similar to the example 1. The results show good agreement with data obtained by Lane Eynone method as shown in Table 2.

TABLE 2

| Measurements by Lane Eynon | Measurements in Example 2 |
|---|---|
| 30.0 | 29.8 |
| 32.5 | 32.5 |
| 35.0 | 35.1 |
| 37.5 | 37.4 |
| 40.0 | 40.1 |

Wherein Lane Eynon method indicates analysis by reduction of Cu ions contained in an alkaline solution with a reducing sugar solution added, and followed by determination of remained Cu ions by titration.

EXAMPLE 3

Figure 3:
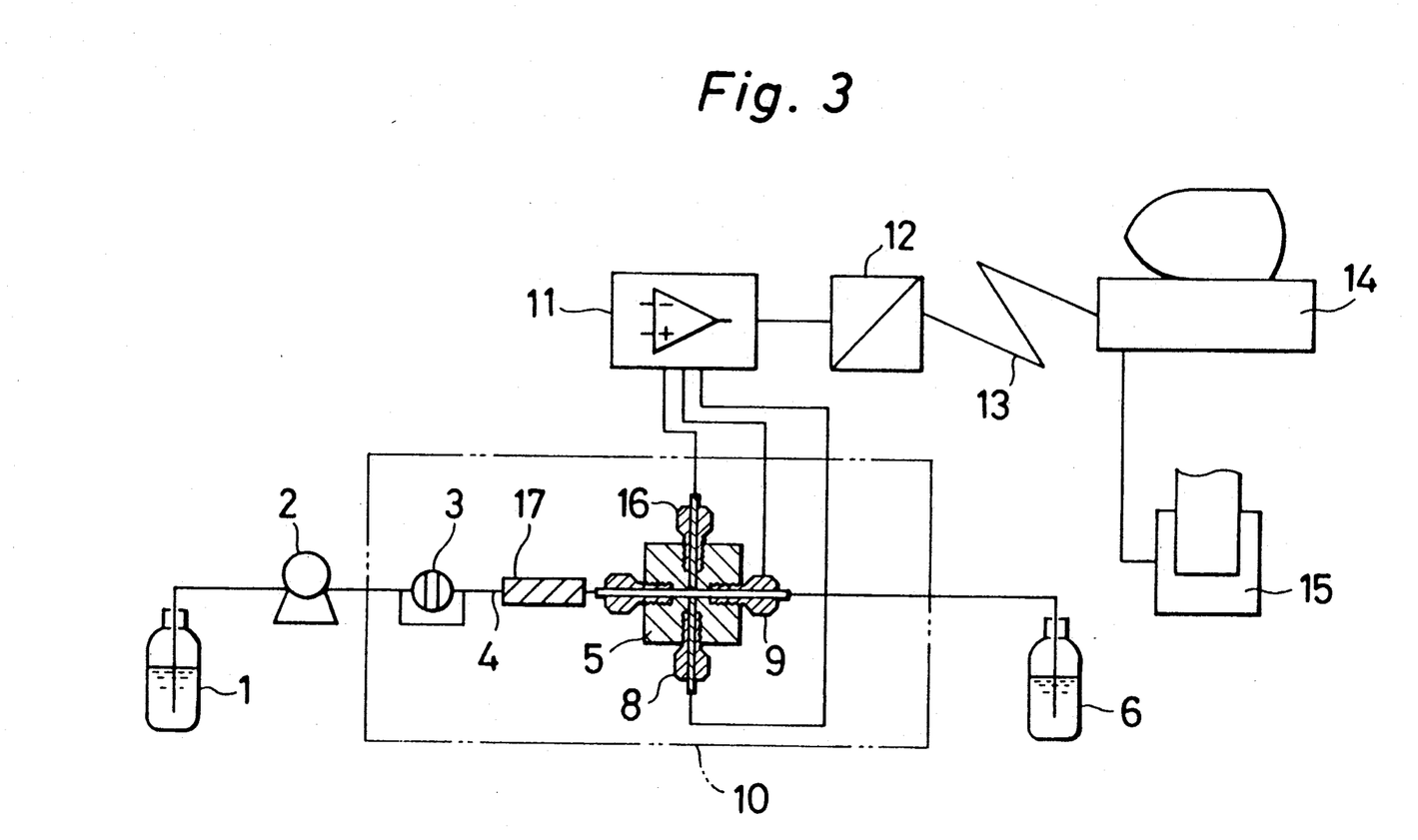
FIG. 3 is a schematic drawing to show the measurement apparatus including a combination of an immobilized enzyme column and an electrode.

The apparatus for measuring glucose including the combination of an immobilized enzyme column and an electrode is shown in FIG. 3. And reference will be made to preparation of the immobilized enzyme column (17) in FIG. 3. Fire brick particles (sieved into 30 to 60 meshes) 150 mg was well dried, and thereon 1 ml of γ-aminopropyltriethoxy silane 10% anhydrous toluene solution was added and allowed to stand for 1 hour. Silane coupling agent was washed well with toluene and ethanol, and then dried at 120° C. for 2 hours. After air cooled, 0.5 ml of 5% glutaraldehyde solution was added, and allowed to stand at room temperature for 1 hour. This carrier was washed well with water. Lastly washed with 100 mM sodium phosphate buffer solution (pH7) and excluded the buffer solution as much as possible. The amino silanated carrier thus obtained was loaded with an enzyme solution containing 10 mg of glucose oxidase (purchased from SIGMA) in a sodium phosphate buffer solution (pH7) and allowed to stand at a room temperature for 1 hour. And then subjected to washing by the buffer solution. The immobilized enzyme carrier thus obtained was filled into a tube made of fluorocarbon resin having the outer diameter: 3 mm, the inner diameter: 2 mm, length: 10 cm.

The immobilized enzyme column (17) was fitted in the apparatus as shown in FIG. 3. Features of the apparatus are nearly the same as in the example 1, wherein an electrode for measuring hydrogen peroxide (16) is equipped with, in place of the glucose measuring electrode.

Analyses were carried out on the same samples as in the example 2, of which results show good agreement with the results by Lane Eynon method as shown below in Table 3.

TABLE 3

| Measurement by Conventional Method | Measurement in Example 3 |
|---|---|
| 30.0 | 30.1 |
| 32.5 | 32.6 |
| 35.0 | 34.9 |
| 37.5 | 37.4 |
| 40.0 | 40.0 |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A method for determining at least one of the average molecular weight, average chain length and dextrose equivalent (DE value) of a carbohydrate sample containing carbohydrates which consist essentially of glucose units, which comprises the steps of:
   (a1) hydrolyzing the carbohydrates contained in a first portion of the carbohydrate sample so that the carbohydrates are hydrolyzed to glucose units,
   (a2) measuring quantitatively the glucose content of the first portion of the sample to obtain a value representative of the total glucose content (Gt) of the sample,
   (b1) reacting the carbohydrates contained in a second portion of the carbohydrate sample with a borohydride salt so that the terminal ends of those carbohydrates which have two adjacent glucose units capable of reduction are reduced to form a malititol structure,
   (b2) hydrolyzing the resulting carbohydrates contained in the second portion of the carbohydrate sample obtained in step (b1) with a hydrolyzing agent so that the carbohydrates in the sample are hydrolyzed to glucose units except for the malititol structure at the terminal ends of the reduced carbohydrates, wherein said hydrolyzing agent is at least one selected from the group consisting of glucosidase and amylase,
   (b3) measuring quantitatively the glucose content of the second portion of the sample to obtain a value representative of the glucose content of the carbohydrates (Gr) of the sample obtained in step (b2), and
   (c) calculating said at least one of the average molecular weight, average chain length and dextrose equivalent (DE value) of the carbohydrate sample based upon the Gt and Gr values of the sample.

2. The method according to claim 1, wherein the hydrolyzing agent is amylase.

3. The method according to claim 2, wherein the amylase is glucoamylase.

4. The method according to claim 1, wherein the hydrolyzing agent is both amylase and glucosidase.

5. The method according to claim 1, wherein the glucose content is measured using an immobilized enzyme electrode for measuring glucose.

6. The method according to claim 5, wherein the immobilized enzyme electrode is an electrode to detect hydrogen peroxide having immobilized thereon glucose oxidase.

7. The method according to claim 1, wherein the glucose content is measured using a combination of an immobilized enzyme column and an electrode for measuring glucose.

8. The method according to claim 7, wherein the immobilized enzyme column is a column being immobilized therein glucose oxidase and the electrode is an electrode to detect hydrogen peroxide.

9. The method according to claim 1, further including a step of measuring quantitatively the free glucose content of an unhydrolyzed portion of the sample to obtain a value representative of the free glucose amount (Gf) of the sample.

10. The method according to claim 9, wherein said amylase is glucoamylase.

11. The method according to claim 9, wherein the hydrolyzing agent is at least one selected from the group consisting of amylase and glucosidase, and the average molecular weight, average chain length or dextrose equivalent of the carbohydrate sample is calculated based upon the Gt, Gr and Gf values of the sample.

12. The method according to claim 11, wherein the average molecule weight (Ma) of the carbohydrates in the sample is calculated using the formula:

$$Ma = 18(19 \times Gt + Gf - Gr)/(Gt - Gr + Gf).$$

13. The method according to claim 11, wherein the average chain length (Dp) of the carbohydrates in the sample is calculated using the formula:

$$Dp = 2 \times Gt/(Gt - Gr + Gf).$$

14. The method according to claim 11, wherein the dextrose equivalent (DE value) of the carbohydrates in the sample is calculated using the formula:

$$DE = 1000(Gt - Gr + Gf)/(19 \times Gt - Gr + Gf).$$

15. The method according to claim 1, wherein the carbohydrate sample contains at least one member selected from the group consisting of a starch; a hydrolysate of a starch; a linear maltooligosaccharide; and derivatives of a starch.

16. The method according to claim 1, wherein the carbohydrates are oligosaccharides or polysaccharides.

17. The method according to claim 1, wherein the carbohydrate sample contains a linear maltooligosaccharide selected from the group consisting of maltose, maltotriose, maltotetraose, maltopentaose, maltohexaose and maltoheptaose.

18. The method according to claim 1, wherein the carbohydrate sample contains a starch derivative selected from the group consisting of ether derivatives, cationic derivatives and carboxy derivatives.

19. An apparatus for determining at least one of the average molecular weight, average chain length and dextrose equivalent (DE value) of a carbohydrate sample containing carbohydrates which consist essentially of glucose units, which comprises:

measuring means for measuring the glucose content of a sample and for generating an electrical current representative of a value corresponding to the glucose content of the sample, wherein the measuring means is an immobilized enzyme electrode or a combination of an immobilized enzyme column and an electrode for measuring glucose, input means for designating the value represented by the electrical current as corresponding to the free glucose content (Gf), total glucose content (Gt) or reduced glucose content (Gr) of the sample, memory means operatively coupled to said input means and said measuring means for storing the value represented by the electrical current as one of the glucose content (Gt), (Gr) and (Gf) of the sample, and processor means operatively coupled to said memory means for calculating the average molecular weight, average chain length or dextrose equivalent of the sample using the values representing the glucose content (Gt), (Gr) and (Gf) of the sample stored in said memory means.

20. The apparatus according to claim 19, wherein the immobilized enzyme column is an electrode to detect hydrogen peroxide having immobilized thereon glucose oxidase.

21. The apparatus according to claim 19, wherein the immobilized enzyme column is a column being immobilized therein glucose oxidase and the electrode is an electrode to detect hydrogen peroxide.

22. The apparatus according to claim 19, wherein the average molecule weight (Ma) of the carbohydrates in the sample is calculated using the predetermined program:

$$Ma = 18(19 \times Gt + Gf - Gr)/(Gt - Gr + Gf).$$

23. The apparatus according to claim 19, wherein the average chain length (Dp) of the carbohydrates in the sample is calculated using the predetermined program:

$$Dp = 2 \times Gt/(Gt - Gr + Gf).$$

24. The apparatus according to claim 19, wherein the dextrose equivalent (DE value) of the carbohydrates in the sample is calculated using the predetermined program:

$$DE = 1000(Gt - Gr + Gf)/(19 \times Gt - Gr + Gf).$$

* * * * *